United States Patent [19]

Vanderpool et al.

[11] Patent Number: 4,727,143

[45] Date of Patent: Feb. 23, 1988

[54] METHOD FOR THE SELECTIVE MANUFACTURE OF N,N'-DIMETHYL PIPERAZINE

[75] Inventors: Steven H. Vanderpool, New Braunfels; Peter S. Morford, Austin, both of Tex.

[73] Assignee: Texaco Inc., White Plains, N.Y.

[21] Appl. No.: 871,941

[22] Filed: Jun. 9, 1986

[51] Int. Cl.$^4$ ............................................. C07D 295/02
[52] U.S. Cl. ........................................ 544/404; 564/479
[58] Field of Search ........................ 544/404; 564/479

[56] References Cited

U.S. PATENT DOCUMENTS

| | | | |
|---|---|---|---|
| 3,037,025 | 5/1962 | Godfrey | 544/404 |
| 3,159,633 | 12/1964 | Lanpdon et al. | 544/404 |
| 3,167,551 | 1/1965 | Weiport | 544/404 |
| 3,249,613 | 5/1966 | Burns et al. | 544/404 |
| 3,697,524 | 10/1972 | Tomalia et al. | 544/404 |
| 3,732,311 | 5/1973 | Baron | 544/404 |
| 4,036,881 | 7/1977 | Brennan et al. | 564/512 |
| 4,105,657 | 8/1978 | Dockner et al. | 544/404 |
| 4,316,840 | 2/1982 | Ford et al. | 564/512 |
| 4,588,842 | 5/1986 | Vanderpool | 564/512 |
| 4,647,664 | 3/1987 | Vanderpool | 564/479 |

FOREIGN PATENT DOCUMENTS 2316358 10/1974 Fed. Rep. of Germany ...... 544/404

OTHER PUBLICATIONS

Vanderpool, CA 101-194142v.

*Primary Examiner*—Donald G. Daus
*Assistant Examiner*—Cecilia Shen
*Attorney, Agent, or Firm*—Jack H. Park; Kenneth R. Priem; Carl G. Ries

[57] ABSTRACT

Piperazine, in solution in methanol may be substantially selectively converted to N,N'-dimethyl piperazine when using a catalyst composed of titania to which from about 0.5 to about 7 wt. % of phosphorous has been thermally chemically bonded in the form of phosphate linkages.

8 Claims, No Drawings

METHOD FOR THE SELECTIVE MANUFACTURE OF N,N'-DIMETHYL PIPERAZINE

BACKGROUND OF THE INVENTION

1. Field of the Invention

This invention relates to a catalytic method for the preparation of N,N'-dimethyl piperazine. More particularly, this invention relates to a catalytic method for the substantially selective manufacture of N,N'-dimethyl piperazine from piperazine and methanol. Still more particularly, this invention is directed to the use of a titania catalyst to which a minor amount of phosphorus has been thermally chemically bonded at the surface thereof in the form of phosphate phosphate linkages to substantially selectively catalyze the conversion of methanol and piperazine to N,N'-dimethyl piperazine.

2. Prior Art

The catalysts used in the practice of the process of the present invention are disclosed in Vanderpool European patent application Ser. No. 83,307,520.3 published Aug. 28, 1984, wherein they are disclosed as useful in promoting the reaction of ethylenediamine with ethanolamine to provide essentially linear polyethylenepolyamine reaction products. Minor quantities of cyclic products are also formed.

It has heretofore been proposed to prepare N,N'-dimethylpiperazine by a variety of techniques. For example, Steele U.S. Pat. No. 2,868,791 discloses a process for the preparation of N,N'-dimethylpiperazine by the pressured reaction of N-methylethanolamine with carbon dioxide. In the example, an aqueous solution of N-methylethanolamine was saturated with carbon dioxide and heated at 160°–170° C. for 20 hours at a pressure of 500–580 psia to provide a crude reaction mixture containing N,N'-dimethylpiperazine.

Godfrey U.S. Pat. No. 3,037,025 discloses a process for the preparation of N-alkyl substituted piperazines such as N,N'-dimethylpiperazine by reacting monoethanolamine with methylamine at an elevated temperature and pressure in the presence of a nickel, copper, chromia hydrogenation catalyst in the presence of hydrogen. There is a similar disclosure in Godfrey U.S. Pat. No. 3,037,025.

Schulze U.S. Pat. No. 4,066,649 discloses a process for the catalytic production of N,N'-(dimethyl) piperazines by reacting a primary 1-amino-2-alkanol such as monoethanolamine with methyl alcohol. The catalyst that is used is a phosphorus containing substance such as acidic metal phosphate, a compound of phosphorus or phosphoric acid, alkyl or aryl phosphate or phosphite esters.

A process for the production of N-alkylated cyclic alkyleneimines such as N-methyl piperazine from an alcohol such as methanol and a cyclic amine such as piperazine is disclosed in Dockner et al. U.S. Pat. No. 4,105,657. The catalyst is a high surface area $SiO_2$/$P_2O_5$ catalyst prepared, for example, by reacting 0.1 to 20% of phosphoric acid with a silic acid hydrogel.

SUMMARY OF INVENTION

It has been surprisingly discovered in accordance with the present invention that methanol and piperazine may be substantially selectively converted to N,N'-dimethyl piperazine when the conversion is catalyzed with a catalyst composed of titania to which from about 0.5 to 7 wt. % of phosphorus has been thermally chemically bonded in the form of phosphate linkages.

DETAILED DESCRIPTION OF THE EMBODIMENT

The feedstocks to be used in accordance with the present invention are methanol and piperazine. Since piperazine is soluble in methanol, the feedstock is suitably utilized in the form of a methanol solution of piperazine. At least 2 mols of methanol should be used per mol of piperazine and, preferably, from about 2 to 20 mols of methanol per mol of piperazine. Still more preferably, about 8 to 12 mols of methanol are used per mol of piperazine.

Reaction Conditions

The reaction of the present invention is conducted utilizing piperazine which is dissolved in methanol so as to form about a 10 to about 50 wt. % methanol solution of piperazine, such as a 20 wt. % methanol solution and which is brought into contact with a catalyst in a batch reactor or in a continuous reactor.

When the reaction is conducted in a batch reactor, the catalyst will preferably be employed in powdered form, whereas when the reaction is conducted on a continuous basis the catalyst is preferably employed in the form of pellets.

The reaction is suitably conducted at a temperature of about 250°–400° C. and, more preferably, at a temperature of about 290° to about 340° C.

The reaction is also preferably conducted at a pressure of about 100 to 3000 psig. and, more particularly, at a pressure of about 200 to about 1500 psig.

When the reaction is conducted on a batch basis, the reaction time may suitably vary from about 0.5 to about 10 hours. When the reaction is conducted on a continuous basis, the feedstock may suitably be passed over a bed of pelleted catalyst at a liquid hourly space velocity (lhsv) of about 0.2 to about 5 volumes of the aqueous solution of the amine feedstock per volume of catalyst per hour. More preferably, the lhsv will be from about 0.5 to about 2.

It is not necessary to use either ammonia or hydrogen as feed components in the practice of the process of the present invention.

Catalyst

The catalyst composition of the present invention is prepared by depositing a phosphorus compound on titania support described in greater detail in copending Vanderpool application Ser. No. 06/564,153 filed Dec. 22, 1983, and entitled "Catalytic Preparation of Linear Polyethylenepolyamines" and in Vanderpool European patent application Ser. No. 83,387,520.3 published Aug. 28, 1984.

Any appropriate water soluble or liquid phosphorus compound can be used as a source of the phosphorus. For convenience, phosphoric acid will normally be used. However, other phosphorus compounds such as phosphoryl chloride ($POCl_3$), phosphorous acid, polyphosphoric acid, phosphorus halides, such as phosphorus bromide, alkyl phosphates and alkyl phosphites such as trimethyl phosphate, triethyl phosphate, trimethyl phosphite, triethyl phosphite, etc. may be utilized. Also, a diamminohydrogen phosphate such as diammonium hydrogen phosphate, $(NH_4)_2HPO_4$, dimethylamino hydrogen phosphate, $(CH_3)_2NH_2PO_4$, diethylaminohydrogen phosphate $(CH_3CH_2)_2NH_2PO_4$, etc. may be used.

A suitable procedure to be used is to heat a liquid containing the liquid or liquefiable phosphorus compound at a temperature of about 100° to about 150° C. and to then add powdered or pelleted titania in an amount about equal to the volume of the heated liquid. This treatment should be continued from about 0.5 to about 5 hours. At the end of that time, the resulting mixture is cooled, decanted to remove excess liquid followed by washing with an amount of water adequate to substantially completely remove unadsorbed liquid. Temperatures above 150° C. can be used, if desired, but there is no particular advantage in doing so.

It will be understood that the phosphorus that is present on a thus-treated catalyst is not present as elemental phosphorus, but rather as phosphorus that is chemically bound, probably as an oxide, to the titania. This is demonstrated by the fact that repeated washing will not remove all of the phosphorus. However, the exact nature of the bonding is not completely understood.

The amount of phosphorus that is bonded or otherwise adheres to the titania is a function of heating and other conditions used in the treating step and is also a function of the chemical identity of the phosphorus compound that is used as a source of phosphorus. Under the treating conditions exemplified above, at least about 0.5 wt % of phosphorus is caused to bond (i.e., permanently adhere) to the titania. There is an upper limit to the amount of phosphorus that bonds to the titania. This upper limit is, as indicated, a function of both the treating conditions and the chemical used as a source of the phosphorus. Normally, the maximum amount of phosphorus that can be caused to bond or otherwise permanently adhere to the titania is within the range of about 7 wt. %.

As a matter of convenience, the normal practice is to use only one chemical as a phosphorus source (e.g., phosphoric acid). However, mixtures of two or more such reagents may be used, if desired.

When the catalyst is to be used in pelleted form, pellets of titania can be impregnated with the phosphorus compound at a temperature of at least about 100° C., there is no absolute need to calcine the catalyst composition before use. However, the pellets can be calcined prior to use, if desired, as a precautionary measure and/or in order to still further improve the physical properties of the pellets. The pellets are suitably calcined at a temperature of about 200° C. to about 800° C. for a period of time within the range of 2 to 24 hours; more preferably at a temperature of about 300° C. to about 600° C. for about 4 to 16 hours.

Other procedures can be used in adding phosphorus to the titania. For example, the pellets can be treated with the phosphorus compound at ambient temperatures or at more modest elevated temperatures of less than about 100° C.

If the treatment is conducted at a temperature of about 100° C. or more, thermal activation will normally have been obtained and it will not be absolutely necessary to perform a calcining operation prior to use. If lower treating temperatures are used, calcining prior to use is normally a desired operation. The calcining operation can be conducted prior to or subsequent to the pelleting step.

In any event, in-situ calcining will occur when the phosphorus-titania composition is used to catalyze the conversion of methanol and piperazine to N,N'-dimethylpiperazine at a temperature of 250° to 400° C.

EXAMPLES

Equipment and Procedures

In all cases, these evaluations were performed in a 100 cc reactor constructed of ⅜ inch stainless steel tubing connected to ⅛ inch feed and effluent lines with swagelok fittings. The reactor tube was situated inside of a 3×3 inch aluminum block which was heated electrically with four 1000 watt strip heaters. Temperature control was achieved with a Thermoelectric controller monitoring thermocouples attached to the skin of the reactor body. The feed was charged to the reactor system with a Beckman 110A L.C. pump. For safety, pressure relief was provided by a 3000 lb. rupture disk assembly although all runs were preformed at atmospheric pressure to minimize bimolecular reactions. The reactor effluent was collected in a glass jug and sampled after the system had lined-out at the proscribed temperature for at least 2.5 hours.

The feedstock consisted of a 20 wt. % solution of piperazine in methanol.

Analysis of the reactor effluent was achieved using an OV-17 column in a Hewlett-Packard 5710A gas chromatograph. Analysis was on a water-free and feed-free basis.

A series of experiments were performed at atmospheric pressure, a reactor pressure of 200 psig. and a reactor pressure of 1300 psig. at the temperatures indicated in Table I, where the results are also reported.

TABLE I

| Example | Press. | Temp. | Conv. | DMP | MMP | Unk. |
|---|---|---|---|---|---|---|
| 1 | Atm | 300 | 85.9 | 52.5 | 41.1 | 1.6 |
| 2 | " | 310 | 91.3 | 59.5 | 33.6 | 0.7 |
| 3 | " | 320 | 97.2 | 68.3 | 21.5 | 1.1 |
| 4 | " | 330 | 99.8 | 79.5 | 2.7 | 2.7 |
| 5 | 200# | 280 | 99.6 | 85.6 | 12.7 | 0.9 |
| 6 | " | 289 | 99.9 | 90.7 | 5.1 | 1.7 |
| 7 | " | 300 | 99.4 | 89.9 | 5.0 | 2.1 |
| 8 | " | 310 | 99.7 | 88.9 | 6.1 | 1.9 |
| 9 | " | 320 | 99.5 | 85.8 | 4.1 | 2.3 |
| 10 | " | 329 | 99.1 | 78.1 | 3.6 | 3.1 |
| 11 | 1300# | 290 | 99.6 | 78.3 | 3.0 | 1.6 |
| 12 | " | 300 | 99.6 | 89.4 | 2.0 | 3.7 |
| 13 | " | 310 | 99.6 | 84.4 | 2.0 | 3.9 |
| 14 | " | 320 | 99.4 | 79.1 | 2.3 | 2.8 |
| 15 | " | 330 | 98.9 | 76.9 | 2.4 | 2.4 |

As can be seen from Table I, the conversion of the methanol and piperazine to N,N'-dimethyl piperazine was not particularly high at atmospheric pressure (except at high temperatures, e.g. 330° C.), but was substantially complete at the higher pressures at temperatures of about 280° C. or more.

The foregoing examples are given by way of illustration only and are not intended as limitations in the scope of this invention, as defined by the appended claims.

What is claimed is:

1. A method for the manufacture of N,N'-dimethyl piperazine which comprises bringing a methanol solution of piperazine comprising about 2 to about 20 mols of methanol per mol of piperazine into contact with a catalyst at a temperature of about 250°–400° C. and a pressure of about 100 to about 3000 psig. for a period of time sufficient to substantially selectively convert at least about 75% of said piperazine to N,N'-dimethyl piperazine, said catalyst comprising titania having from about 0.5 to about 7 wt. % of phosphorus thermally chemically bonded to the surface thereof in the form of phosphate bonds.

2. A method as in claim 1 wherein the methanol solution contains about 4 to 10 mols of methanol per mol of piperazine.

3. A method as in claim 2 wherein the reaction temperature is within the range of about 200° to 340° C.

4. A method as in claim 3 wherein the reaction pressure is within the range of about 200 to about 1500 psig.

5. A method for the manufacture of N,N'-dimethyl piperazine which comprises bringing a 10 to 50 wt. % solution of piperazine in methanol consisting essentially of about 2 to about 20 mols of methanol per mol of piperazine into contact with a catalyst at a temperature of about 250°–400° C. and a pressure of about 100 to about 3000 psig. for a period of time sufficient to substantially selectively convert about 76 to about 90% of said piperazine to N,N'-dimethyl piperazine, said catalyst consisting essentially of titania having from about 0.5 to about 7 wt. % of phosphorus thermally chemically bonded to the surface thereof in the form of phosphate bonds.

6. A method as in claim 5 wherein the solution consists essentially of about 4 to about 10 mols of methanol per mol of piperazine and the reaction is conducted at a temperature of about 290° to 340° C. and a pressure within the range of about 200 to about 1500 psig.

7. A method as in claim 6 wherein the reaction is conducted in a batch reactor for a reaction time within the range of about 0.5 to about 10 hours in the presence of powdered catalyst.

8. A method as in claim 6 wherein the reaction is conducted in a continuous reactor in the presence of a bed of pelleted catalyst and the feedstock is passed over the bed of catalyst at a liquid hourly space velocity of about 0.2 to about 5 volume of feedstock per volume of catalyst per hour.

* * * * *